(12) United States Patent
Urman et al.

(10) Patent No.: US 10,360,700 B2
(45) Date of Patent: Jul. 23, 2019

(54) INTERPOLATION OF DYNAMIC THREE-DIMENSIONAL MAPS

(71) Applicant: BIOSENSE WEBSTER (ISRAEL) LTD., Yokneam (IL)

(72) Inventors: Roy Urman, Karkur (IL); Meir Bar-Tal, Haifa (IL); Yaniv Ben Zriham, Binyamina (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 0 days.

(21) Appl. No.: 15/041,385

(22) Filed: Feb. 11, 2016

(65) Prior Publication Data

US 2017/0236311 A1    Aug. 17, 2017

(51) Int. Cl.
| | |
|---|---|
| *G06T 11/20* | (2006.01) |
| *A61B 5/044* | (2006.01) |
| *A61B 5/04* | (2006.01) |
| *A61B 5/0452* | (2006.01) |
| *A61B 5/042* | (2006.01) |

(52) U.S. Cl.
CPC ............ *G06T 11/206* (2013.01); *A61B 5/044* (2013.01); *A61B 5/04012* (2013.01); *A61B 5/0452* (2013.01); *A61B 5/0422* (2013.01); *G06T 2210/41* (2013.01)

(58) Field of Classification Search
CPC ... G06T 11/206; G06T 2210/41; A61B 5/044; A61B 5/04012; A61B 5/0452; A61B 5/0422
See application file for complete search history.

(56) References Cited

U.S. PATENT DOCUMENTS

| | | |
|---|---|---|
| 6,301,496 B1 | 10/2001 | Reisfeld |
| 8,456,182 B2 | 6/2013 | Bar-Tal et al. |

(Continued)

OTHER PUBLICATIONS

European Search Report dated Jul. 4, 2017 from corresponding European Patent Application No. 17155561.8.

(Continued)

*Primary Examiner* — Chong Wu
(74) *Attorney, Agent, or Firm* — Lewis Roca Rothgerber Christie LLP

(57) ABSTRACT

A method, including acquiring initial signals from selected positions in a heart, computing respective initial local values of a signal propagation metric at the selected positions, and interpolating the initial local values between the selected positions to compute initial interpolated values of the signal propagation metric at intermediate positions, between the selected positions. The method further includes acquiring subsequent signals from the positions, computing respective subsequent local values of the signal propagation metric at the selected positions, and spatially interpolating the subsequent local values of the signal propagation metric between the selected positions to compute subsequent interpolated values of the signal propagation metric at the intermediate positions. A map of the signal propagation metric is displayed, and when the subsequent interpolated values exceed a bound defined with respect to the initial interpolated values, an indication is provided on the map that the bound has been exceeded.

10 Claims, 6 Drawing Sheets

(56) References Cited

U.S. PATENT DOCUMENTS

| | | | |
|---|---|---|---|
| 2010/0222671 A1* | 9/2010 | Cohen | A61B 5/0044 600/424 |
| 2013/0006131 A1* | 1/2013 | Narayan | A61B 5/042 600/508 |
| 2013/0190834 A1 | 7/2013 | Ghosh et al. | |
| 2014/0200575 A1* | 7/2014 | Spector | A61B 5/04014 606/40 |
| 2015/0250399 A1 | 9/2015 | Laughner et al. | |

OTHER PUBLICATIONS

Ni, Quan et al., "Three-Dimensioonal Activation Mapping in Ventricular Muscle: Interpolation and Approximation of Activation Times", Annals of Biomedical Engineering, Sep. 1, 1999, pp. 617-626, vol. 27, No. 5.

Yilmaz, Bülent et al., "Usage of spline interpolation in catheter-based cardiac mapping", Turkish Journal of Electrical Engineering and Computer Sciences, Jan. 1, 2010, pp. 989-1002, vol. 18, No. 6.

* cited by examiner

INTERPOLATION OF DYNAMIC THREE-DIMENSIONAL MAPS

FIELD OF THE INVENTION

The present invention relates generally to representing data graphically, and specifically to mapping of three-dimensional parameters that are changing with time.

BACKGROUND OF THE INVENTION

Intra-cardiac ECG (electrocardiograph) signals may be used to track the progress of a cardiac procedure, such as a ablation procedure. Typically, the signals are acquired by inserting a catheter with one or more electrodes into the heart undergoing the procedure. The electrodes acquire electropotentials developed in the heart, at the positions where the electrodes contact the heart, as the heart beats. The signals may then be analyzed, and results of the analysis may be used to inform a medical professional performing the procedure of the progress of the procedure.

The description above is presented as a general overview of related art in this field and should not be construed as an admission that any of the information it contains constitutes prior art against the present patent application.

SUMMARY OF THE INVENTION

An embodiment of the present invention provides a method, including:

acquiring an initial set of electrical signals from selected positions in a heart of a subject;

computing, based on the electrical signals in the initial set, respective initial local values of a signal propagation metric at the selected positions;

spatially interpolating the initial local values of the signal propagation metric between the selected positions to compute initial interpolated values of the signal propagation metric at intermediate positions, between the selected positions;

acquiring a subsequent set of electrical signals from the selected positions;

computing, based on the electrical signals in the subsequent set, respective subsequent local values of the signal propagation metric at the selected positions;

spatially interpolating the subsequent local values of the signal propagation metric between the selected positions to compute subsequent interpolated values of the signal propagation metric at the intermediate positions;

generating and displaying a map of the signal propagation metric, including the subsequent interpolated values at the intermediate positions; and when the subsequent interpolated values exceed a bound defined with respect to the initial interpolated values, providing an indication on the map that the bound has been exceeded.

In a disclosed embodiment the signal propagation metric includes a local activation time of the heart.

In a further disclosed embodiment there are no intervening sets of electrical signals between the subsequent set and the initial set.

In a yet further disclosed embodiment the method includes:

acquiring a prior set of electrical signals from the selected positions prior to the initial set;

computing, based on the electrical signals in the prior set, respective prior local values of the signal propagation metric at the selected positions;

spatially interpolating the prior local values of the signal propagation metric between the selected positions to compute prior interpolated values of the signal propagation metric at the intermediate positions, and wherein the bound is defined with respect to the initial interpolated values and to the prior interpolated values.

Typically, there are no intervening sets of electrical signals between the prior set and the initial set.

In an alternative embodiment the signal propagation metric includes a local activation time (LAT) of the selected positions. If there is a time $\Delta T$ between the initial set and the subsequent set, the bound may be exceeded when a difference between the LAT at a given selected position of the initial set and the LAT at the given selected position of the subsequent set exceeds $\Delta T$.

In a further alternative embodiment the signal propagation metric cycles in a preset temporal direction, and the bound is exceeded when the subsequent interpolated values cycle with respect to the initial interpolated values in a direction counter to the preset temporal direction.

There is further provided, according to an embodiment of the present invention, apparatus, including:

a screen configured to display a map of a signal propagation metric; and a processing unit, configured to:

acquire an initial set of electrical signals from selected positions in a heart of a subject, compute, based on the electrical signals in the initial set, respective initial local values of a signal propagation metric at the selected positions, spatially interpolate the initial local values of the signal propagation metric between the selected positions to compute initial interpolated values of the signal propagation metric at intermediate positions, between the selected positions, acquire a subsequent set of electrical signals from the selected positions, compute, based on the electrical signals in the subsequent set, respective subsequent local values of the signal propagation metric at the selected positions, spatially interpolate the subsequent local values of the signal propagation metric between the selected positions to compute subsequent interpolated values of the signal propagation metric at the intermediate positions;

generate and display on the screen the map of the signal propagation metric, including the subsequent interpolated values at the intermediate positions, and when the subsequent interpolated values exceed a bound defined with respect to the initial interpolated values, provide an indication on the map that the bound has been exceeded.

The present invention will be more fully understood from the following detailed description of the embodiments thereof, taken together with the drawings in which:

DETAILED DESCRIPTION OF EMBODIMENTS

Overview

Figure 1:
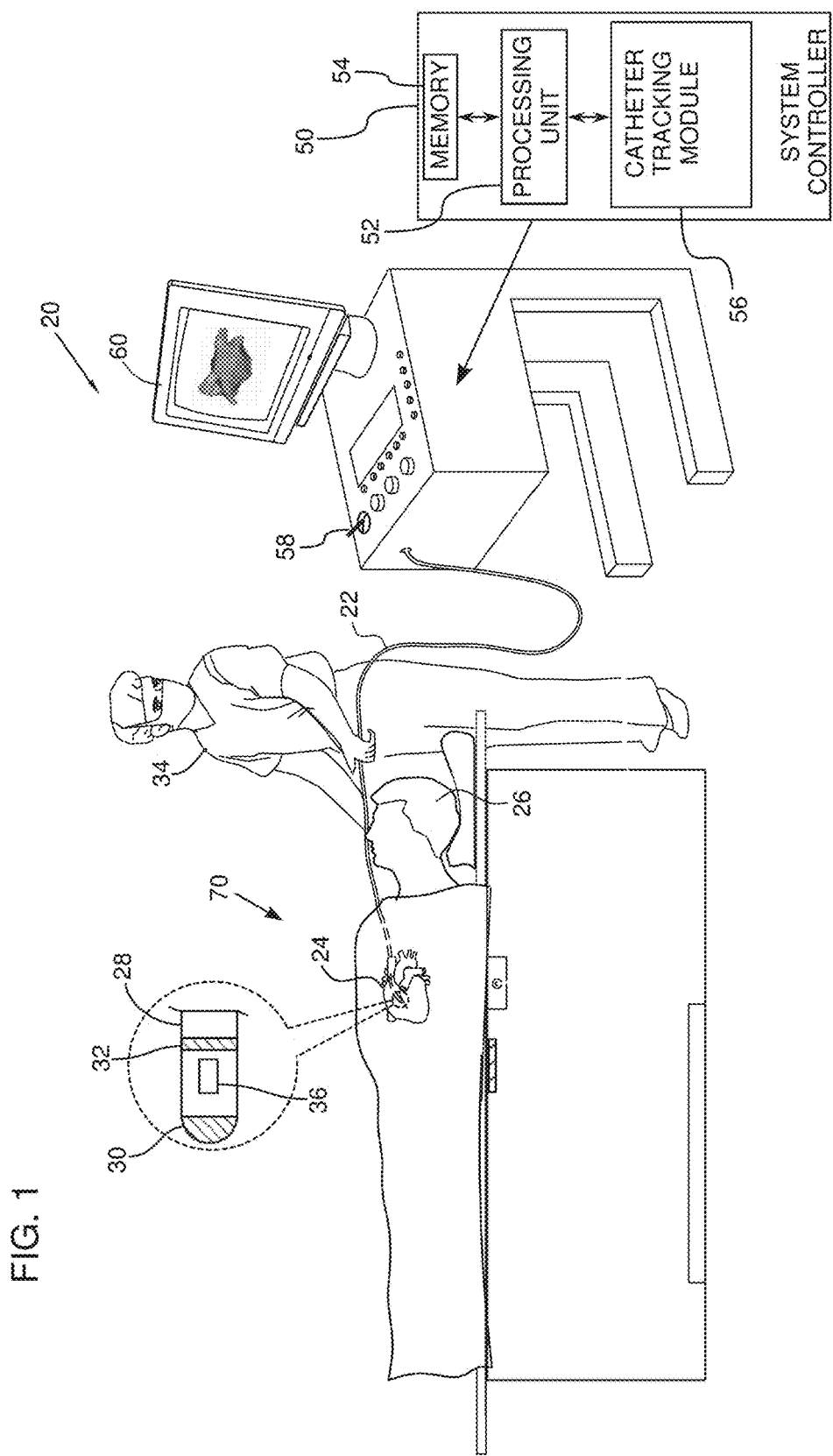
FIG. 1 is a schematic, pictorial illustration of a data acquisition system, according to an embodiment of the present invention.

In order to track the behavior of the heart of a subject, sets of time-varying electrical signals may be acquired from different selected positions in the heart, by positioning electrodes at those positions. From the electrical signals a signal propagation metric, such as a local activation time, may be computed for the selected positions at any given instant in time, and the metric for each of the signals in the set may be used to assess the heart behavior. In order to improve the assessment values of the metric may be calculated for positions intermediate the selected positions, by spatial interpolation between those positions for the instant of time considered. However, such spatial interpolation may lead to incorrect results, particularly if the heart is not beating in a sinus rhythm.

Embodiments of the present invention overcome the problem by comparing spatial interpolations of the metric between different instances of time. For an initial instance an initial set of signals is acquired at the selected positions referred to above, the signal propagation metric is computed based on the signals, and initial interpolated values of the metric for positions intermediate the selected positions are calculated by spatial interpolation between the selected positions.

The procedure is repeated for a subsequent instance, so as to derive subsequent interpolated values of the metric for the intermediate positions.

A map of the signal propagation metric is generated and displayed, the map including metric values derived from the signals acquired at the selected positions, as well as the subsequent interpolated values at the intermediate positions. The values are typically indicated by different colors within a predefined spectrum of colors.

The subsequent interpolated values may exceed a bound defined with respect to the initial interpolated values. For example, if the metric comprises a local activation time (LAT), and the LAT of the initial value is −100 ms, the subsequent value cannot be −50 ms unless two conditions are true: there has been an intermediate value of 0 ms, and there has been sufficient time between the initial and subsequent instances for the LAT change to have occurred. When such a bound is exceeded, a visual indication is provided on the map, typically at the intermediate positions where the bound is exceeded. The visual indication may be a color, such as black or white, that is not in the predefined spectrum of colors referred to above.

The analysis described above is typically used during a playback of previously recorded sets of the electrical signals described above, in order for a physician to make an overall assessment of the condition of a heart, typically prior to performing a cardiac procedure such as local ablation of a section of the heart. However, the analysis may also be implemented in a virtually real-time situation, such as during an ablation procedure, albeit typically with a delay of one or more heartbeats to enable the analysis to be performed.

Detailed Description

Reference is now made to FIG. 1, which is a schematic, pictorial illustration of a data acquisition and playback system 20, according to an embodiment of the present invention. As is explained below, system 20 may be used to interpolate between sequences of data that have been acquired at respective sequences of time, and that are subsequently "played back" to an operator of the system. While it will be understood that system 20 may be used for substantially any such sequences of data, in the following description, for clarity and simplicity, system 20 is assumed to be applied to electrocardiograph (ECG) data that has been acquired during a medical procedure on a heart of a subject.

In system 20, a catheter 22 is inserted into a lumen, such as a chamber of a heart 24 of a subject 26 wherein a medical procedure, such as ablation of the heart tissue, is to be performed. At a distal end 28 of the catheter there are typically a plurality of electrodes, and by way of example two electrodes 30, 32 are shown in the figure. Typically, the distal end comprises a larger number of electrodes, but for clarity and simplicity, such larger number is not shown in the diagram. As is explained below, at least one of the electrodes at the distal end, herein assumed to be electrode 30 at the tip of the distal end, is used by system 20. The catheter is manipulated by a medical practitioner 34 during the procedure, so as to position electrodes 30, 32 in desired locations.

Typically, electrodes at the distal end, including electrodes 30 and 32, may perform multiple functions. For example, an electrode may be configured to perform ablation of tissue of the heart, and/or to act as a source electrode for a distal end tracking system operating by measuring currents from the electrode. In the description hereinbelow, except where otherwise indicated, electrodes 30 and 32 are assumed to acquire electrical signals, herein also termed ECG potentials, of heart 24. Depending on the procedure being performed, the distal end may comprise other elements. By way of example distal end 28 comprises a position sensor 36 which, in response to magnetic fields from radiators (not shown in the figure) external to patient 26, generates signals which may be analyzed to give the location and orientation of the distal end. U.S. Pat. No. 8,456,182 to Bar-Tal et al., which is incorporated herein by reference, describes a system using both magnetic field measurements and currents from a catheter electrode to track the catheter.

The functioning of system 20 is managed by a system controller (SC) 50, comprising a processing unit 52 communicating with a memory 54, wherein is stored software for operation of system 20. The analysis of the signals from sensor 36 may be performed by processing unit 52 communicating with a catheter tracking module 56. Controller 50 is typically an industry-standard personal computer (PC) comprising a general-purpose computer processor. However, in some embodiments, at least some of the functions of the controller are performed using custom-designed hardware and software, such as an application specific integrated circuit (ASIC) or a field programmable gate array (FPGA). Controller 50 is typically operated by practitioner 34 using a pointing device 58 and a screen 60, which enable the practitioner to set parameters of system 20. Screen 60 typically also presents results of the procedure to the medical practitioner.

The software in memory 54 may be downloaded to the controller in electronic form, over a network, for example. Alternatively or additionally, the software may be provided on non-transitory tangible media, such as optical, magnetic, or electronic storage media.

Figure 2:
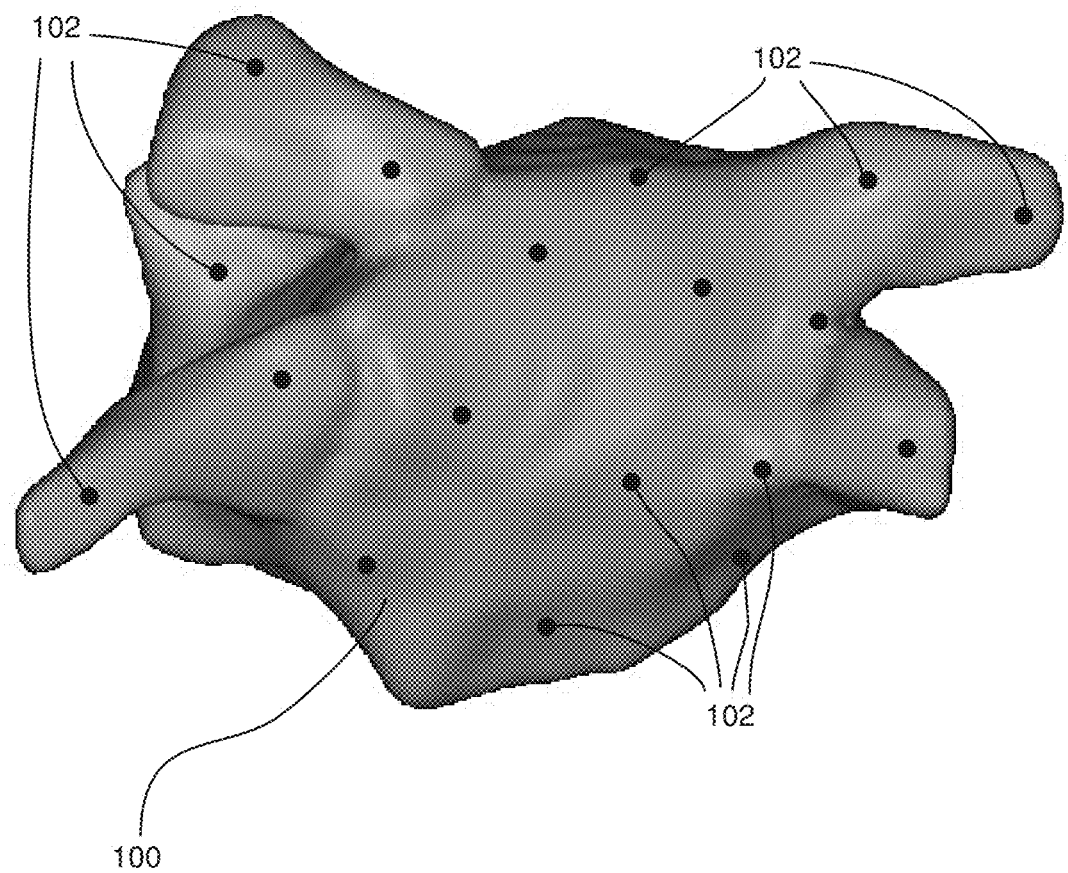
FIG. 2 is a schematic illustration of a map of data presented on a display, according to an embodiment of the present invention.

FIG. 2 is a schematic illustration of a map 100 of data presented on screen 60, according to an embodiment of the present invention. In the following description, for clarity and by way of example, the data presented in map 100 is assumed to comprise values of local activation times (LATs), of a chamber of heart 24, which are incorporated into a three-dimensional (3D) chart of the chamber. However, in general, the data presented in map 100 may comprise any signal propagation metric derived from acquired signals, such as a value and/or a time of a local turning point of the signal, or a function of such a value or time.

The measurements for the chart, i.e., the 3D values of points on the wall of the chamber, may have been determined prior to the measurements of the LATs. Alternatively, the 3D measurements of the wall of the chamber may be determined at substantially the same time as the LATs are measured.

The LAT values are typically represented by different colors, that are incorporated into the 3D chart of the chamber, to produce map 100. In FIG. 2 the different colors are shown as different gray scale levels.

The LAT values of any point on the walls of the chamber vary according to the beating of heart 24. For any particular instance the LAT values are typically measured relative to a fiducial, for example, the time of a predefined portion of the QRS complex detected by a catheter placed in the coronary sinus (CS) of the heart.

To acquire the LAT data for map 100, a plurality of electrodes, such as electrodes 30, 32 and other electrodes not shown in FIG. 1, may be placed in contact at known positions with the wall of the chamber. ECG signals from the electrodes are recorded, and analysis of the recorded ECG signals provides, for any given instance, the values of the LAT for each of the known positions. Thus, for any given instance, there is a set of LATs at the known positions. FIG. 2 illustrates examples of known positions 102 at which ECG signals are recorded. Typically, there are approximately 10-100 or even more known positions 102, corresponding to the number of electrodes recording the signals.

To determine values of LATs for other locations of the walls of the chamber, i.e., at locations of the walls that are not directly measured by the electrodes and that are intermediate the known positions, embodiments of the present invention use interpolation. The interpolation is typically assumed to be implemented during a playback phase of the operation of system 20, and uses two stages of interpolation, which are described with respect to FIGS. 3 and 4.

Figure 3A:
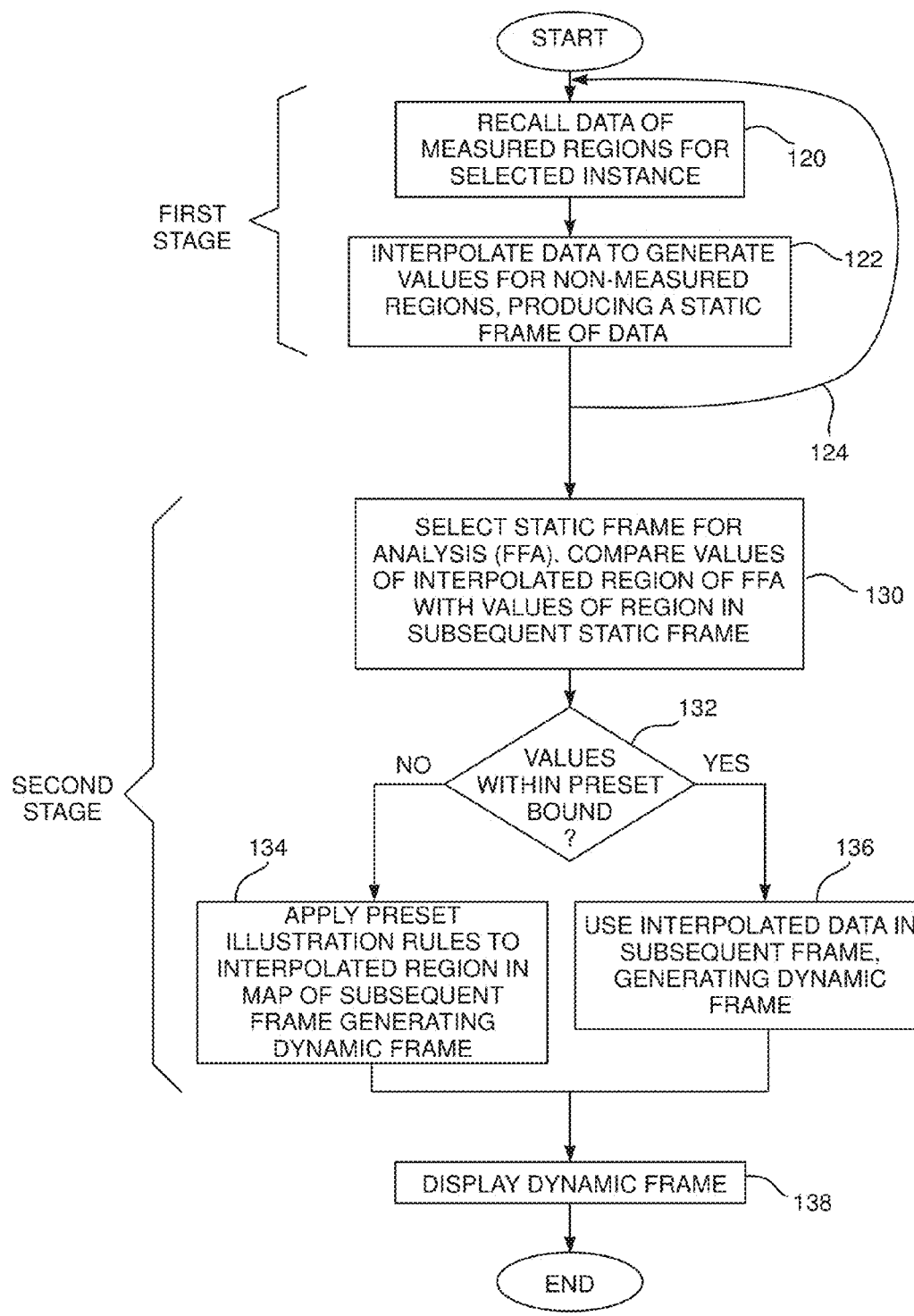
FIG. 3A is a flowchart of steps performed in analyzing acquired data, according to an embodiment of the present invention.
Figure 3B:
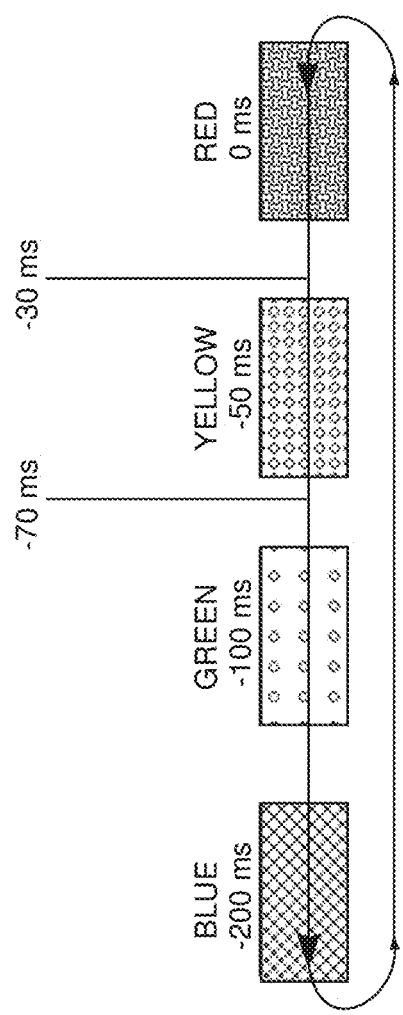
FIG. 3B is a schematic timing diagram of the data, according to an embodiment of the present invention.
Figure 4:
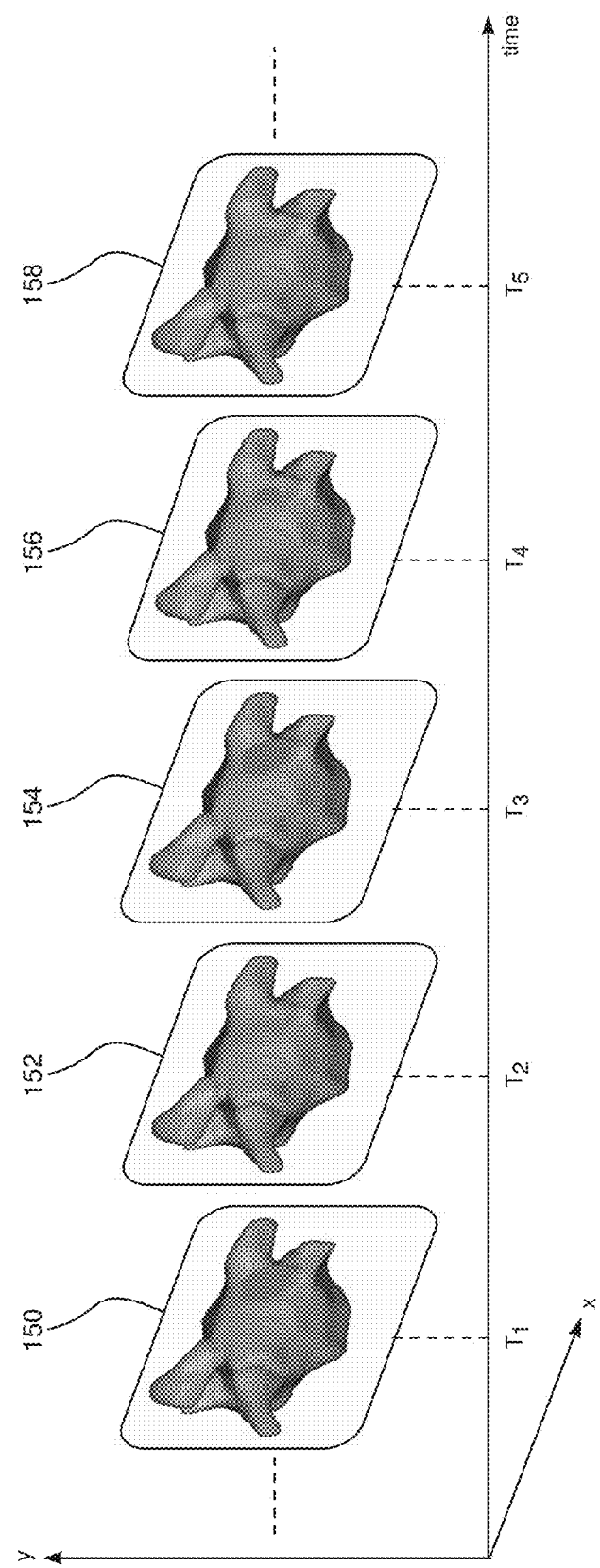
FIG. 4 pictorially illustrates a sequence of static data frames, according to embodiments of the present invention.

FIG. 3A is a flowchart of steps performed by controller 50 in analyzing acquired data, FIG. 3B is a schematic timing diagram of the data, and FIG. 4 is a schematic illustration of sets of data generated by the controller, according to embodiments of the present invention. The steps of the flowchart are arranged in a first stage of interpolation followed by a second stage of interpolation. While in the following description the flowchart steps are assumed to be performed on measurements derived from a sequence of sets of ECG signals that have been recorded at some time prior to implementation of the flowchart, it will be understood that the flowchart may also be implemented in a substantially real-time situation, albeit with a delay of the order of one heartbeat.

Each set of ECG signals is, as is described above, acquired by electrodes in heart 24, and each ECG signal in the set is analyzed to provide a signal propagation metric, herein assumed to be an LAT data value, for the position of its acquiring electrode. Thus each set of ECG signals generates a respective set of measured LAT values for a given instance in time of the signals. The flowchart steps are performed on a sequence of such sets of LAT values, generated from a corresponding sequence of time instances.

The first stage of interpolation comprises a data recall step 120 and an interpolation step 122. In step 120 the controller recalls LAT values, for a given instance, that have been stored and acquired at known electrode positions. In interpolation step 122 the controller spatially interpolates between the known positions, to determine estimated LAT values for locations intermediate the known positions. The interpolation is typically linear spatial interpolation, but may comprise any form of spatial interpolation known in the art. In some embodiments the interpolation may use known conduction velocities at the positions of the electrodes, as well as at positions intermediate the electrodes. In some embodiments the LAT values for the known positions may be assigned respective indices indicative of the accuracy and/or the reliability of the value, and the indices may be used as weights in implementing the interpolation. The combination of the known position LAT values and the interpolated LAT values, for a given instance, is herein termed a static frame of data.

As indicated by an arrow 124, the controller repeats the procedure of steps 120 and 122 for all instances in the sequence being analyzed, to generate respective static frames of the LAT data.

FIG. 4 pictorially illustrates a sequence of static frames generated after step 122 has completed. By way of example, five static frames 150, 152, 154, 156, and 158 are shown in FIG. 4, but the sequence of static frames generated by the first stage of interpolation typically comprises hundreds or thousands of frames. In one embodiment a static frame is generated every 1 ms. In an alternative embodiment a static frame is generated every 5 ms. The sequence has been positioned relative to a time axis, since successive static frames are for successive instances, herein assumed to occur at successive times $T_1, T_2, T_3, T_4, T_5$. While each static frame comprises a group of LAT values, the group may typically be used to generate an image, such as map 100. Thus, in FIG. 4, each static frame has been represented as an image presented on screen 60. However, it will be understood that, rather than presenting static frames as illustrated in FIG. 4, embodiments of the present invention present other frames, herein termed dynamic frames, on screen 60, as is explained below.

Returning to the flowchart, in a comparison step 130, which is a first step of the second stage of interpolation, the controller selects a static frame, from those frames produced in step 122, for further analysis. Within the selected frame for analysis (FFA) there are typically a number of regions having spatially interpolated LAT values. For each of these regions, the controller compares the values of the interpolated LAT values of the selected static FFA with the LAT values of the corresponding region of a static frame subsequent to the selected FFA. The selected FFA is also herein termed the initial static frame.

In the comparison, for each region where there is interpolated data, the controller evaluates if the interpolated values of the subsequent static FFA are within a bound, which is structured to eliminate inconsistencies, typically timing inconsistencies, between the interpolated data of the initial static frame and the interpolated data of the subsequent static frame.

FIG. 3B is a schematic timing diagram of the data for a region, using LAT values. The diagram illustrates the fact that typically the LAT values for the region cycle from a value of 0 ms (red) through −50 ms (yellow), −100 ms (green), and −200 ms (blue). At the −200 ms point in time there is a new heartbeat, so that the LAT value begins again at 0 ms (red). The cyclic nature of the data is apparent when data is replayed, with short time periods between sequential frames of data.

The symbol ΔT represents the time period between frames, and this value can be selected in the playback process of the frames. Typical values of ΔT for short time periods between frames are 1 ms or 5 ms, and in these cases the color progression for any particular region is apparent as red through yellow, green, then blue, and then red. If the cyclical aspect between sequential frames is not maintained, e.g. if a region changes from green to yellow, then the bound referred to above is broken. Similarly, even if the cyclical aspect is maintained, but the change in LAT value is too fast or too slow, then the bound is also broken. For example, for the case of ΔT being 1 ms, then a change of 10 ms of LATs between consecutive frames may be considered too great, breaking the bound. As a second example, for the case of ΔT being 10 ms, then a change of 0 ms of LATs between consecutive frames may be considered too small, breaking the bound. The values of the changes of 10 ms and 0 ms are exemplary, and may be set by practitioner 34.

While the value of ΔT is typically selected to be small (such as 1 ms and 10 ms exemplified above), embodiments of the present invention encompass larger values of ΔT. A general expression where the bound referred to above is exceeded is given by expression (1) below.

Assume that for a given region the interpolated LAT value of the initial frame is LAT(T1) and the interpolated LAT value of the subsequent static frame is LAT(T2). In this case the interpolated values are invalid, i.e., exceed the bound, if the following expression holds:

$$|LAT(T1)-LAT(T2)|<\Delta T \quad (1)$$

where LAT(T1), LAT(T2)≤0.

Typically, the value for ΔT in expression (1) may be allowed to vary within an error limit, for example ±10%. Thus, if in a first case LAT(T1) is −70 ms, LAT(T2) is −30 ms, as illustrated in FIG. 3B, and ΔT is 20 ms, then expression (1) does not hold and the bound is exceeded. However, if in a second case LAT(T1) is −70 ms, LAT(T2) is −60 ms, and ΔT is 20 ms, then expression (1) does hold, i.e., is valid.

Another factor that may be used to determine the bound is a refractory period of the tissue i.e., a time period, typically in an approximate range of 60 ms-100 ms, during which the tissue is incapable of responding.

In a decision step 132, the controller proceeds according to the evaluation in step 130. If the evaluation is outside the bound, such as in the first case presented above, the flowchart continues to a first map presentation step 134. In step 134 the interpolated data of the subsequent static frame may be replaced by a visual indication that the interpolated data is not within acceptable limits. For example the outside-bound interpolated data may be replaced by a colored region, the color being selected so as not to be in the spectrum of colors used for representing the LAT values. For example, the color could be black, grey, or white. In some embodiments, the visual indication may differ depending on the manner in which the bound is exceeded.

If in decision step 132 the evaluation is within the bound, such as in the second case presented above, the flowchart continues to a second map presentation step 136. In step 136 the interpolated data of the subsequent static frame is used as is. Alternatively, the controller may apply the interpolated data of the initial static frame to adjust values of the interpolated data of the subsequent static frame, for example by averaging, typically in a weighted manner, the two sets of interpolated data.

Implementation of steps 134 and 136 results in production of a dynamic frame of data, i.e., a frame of data where data of a given static frame has been compared with data of a subsequently acquired static frame. Depending on the result of the comparison, the data of the subsequent static frame may be changed to produce the dynamic frame. Typically controller 50 stores the dynamic frame produced in steps 134 or 136 for later display.

In a final step 138 of the flowchart, the dynamic frame generated in step 134 or step 136 is displayed on screen 60.

The flowchart of FIG. 3 assumes that spatially interpolated values of a given static frame of data are compared to spatially interpolated values of a subsequent static frame of data, and that, depending on the results of the comparison, values of the subsequent data frame may be altered. Embodiments of the present invention include other types of comparison between frames of data produced at different times.

For example, rather than a given static frame of data being compared with one subsequent static data frame, the comparison in step 130 may comprise comparison with more than one subsequent static frame of data. Alternatively or additionally, the comparison in step 130 may comprise comparison of a given static data frame with one or more prior static data frames, as well as with one or more subsequent static data frames. Furthermore, in some embodiments there may be one or more intervening frames between the compared static frames where the LAT value is 0 ms.

In all cases, one of ordinary skill in the art will be able to adjust the definition of the bound used in steps 130 and 132, typically by weighting the values of the prior and/or subsequent data, to reflect the different types of comparison used.

Figure 5:
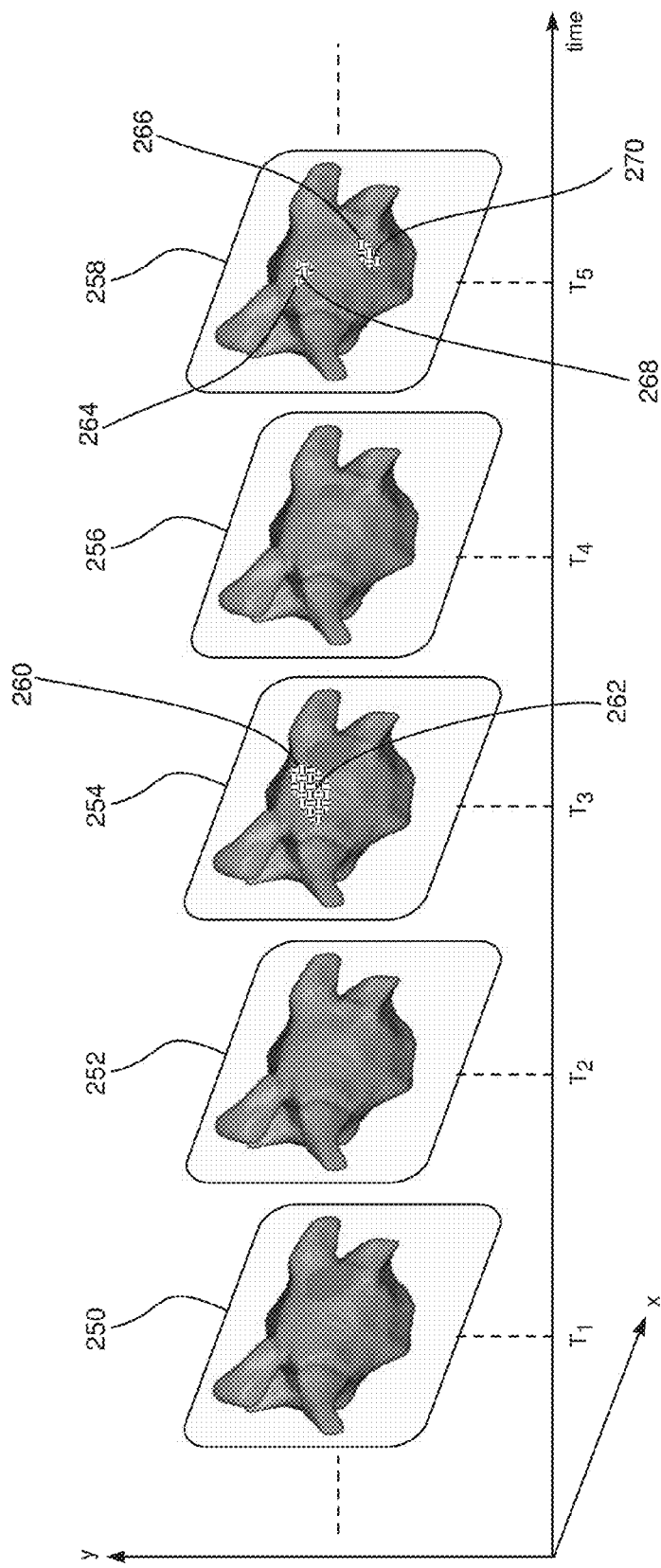
FIG. 5 pictorially illustrates a sequence of dynamic data frames, according to an embodiment of the present invention.

FIG. 5 pictorially illustrates a sequence of dynamic frames generated after step 134 or step 136 has completed, according to an embodiment of the present invention. Dynamic frames 250, 252, 254, 256, and 258 respectively correspond to static frames 150, 152, 154, 156, and 158 of FIG. 4, are produced after each of the static frames has been analyzed in the flowchart of FIG. 3, and are displayed on screen 60 on implementation of step 138 of the flowchart.

By way of example, frames 250, 252, and 256 are assumed to have been generated in step 136, so that the frames are respectively generally similar to frames 150, 152, and 156. Frame 254 is assumed to have been generated in step 134, wherein after the analysis of the step a region 260 has been found to be outside the bound defined in step 130, and a visual indication 262 has been incorporated into the region. In addition frame 258 is also assumed to have been generated in step 134. In this case a region 264 and a region 266 have been found to be outside the defined bound, and visual indications 268 and 270 have respectively been incorporated into these regions.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. An electrophysiology method, comprising:
acquiring an initial set of electrical signals from tissue at selected positions in a heart of a subject, the electrical signals being representative of tissue conductivity;
determining, based on the electrical signals in the initial set, respective initial local values of a signal propagation metric at the selected positions for an initial time;
spatially interpolating the initial local values of the signal propagation metric between the selected positions to determine initial interpolated values of the signal propagation metric at intermediate positions, between the selected positions, for the initial time;
acquiring a subsequent set of electrical signals from the tissue at the selected positions;
determining, based on the electrical signals in the subsequent set, respective subsequent local values of the signal propagation metric at the selected positions for a subsequent time;
spatially interpolating the subsequent local values of the signal propagation metric between the selected positions to determine subsequent interpolated values of the signal propagation metric at the intermediate positions, for the subsequent time;
generating an initial static frame based on the initial local values and the initial interpolated values;
generating a subsequent static frame based on the subsequent local values and the subsequent interpolated values;
generating dynamic frames based on the initial and subsequent static frames in accordance with a rate of static frame generation, comprising providing a visual indication in the dynamic frames when a subsequent interpolated value exceeds a bound defined by the rate of static frame generation, wherein the bound is exceeded when a difference between an initial interpolated value of an intermediate position of the initial time and a subsequent interpolated value at the same intermediate position of the subsequent time exceeds the rate of static frame generation; and
energizing an ablation electrode to ablate tissue at a location of the heart to alter the tissue conductivity at the location based on the dynamic frames.

2. The method of claim 1, wherein the signal propagation metric comprises a local activation time (LAT) of the selected positions.

3. The method according to claim 1, wherein there are no intervening sets of electrical signals between the subsequent set and the initial set.

4. The method according to claim 1, further comprising:
acquiring a prior set of electrical signals from the selected positions;
determining, based on the electrical signals in the prior set, respective prior local values of the signal propagation metric at the selected positions for a prior time;
spatially interpolating the prior local values of the signal propagation metric between the selected positions to determine prior interpolated values of the signal propagation metric at the intermediate positions for the prior time;
generating a prior static frame based on the prior local values and the prior interpolated values; and
generating dynamic frames based on the initial and prior static frames, including providing a visual indication in the dynamic frames when an interpolated value exceeds a bound defined by the rate of static frame generation, wherein the bound is defined with respect to the initial interpolated values and the prior interpolated values, wherein the bound is exceeded when a difference between an initial interpolated value of an intermediate position of the initial time and a prior interpolated value at the same intermediate position of the prior time exceeds the rate of static frame generation.

5. The method according to claim 4, wherein there is no intervening set of electrical signals between the prior set and the initial set.

6. An electrophysiology apparatus, comprising:
a display screen; and
a controller having a processor, the controller configured to:
acquire an initial set of electrical signals from tissue at selected positions in a heart of a subject, the electrical signals being representative of tissue conductivity;
determine, based on the electrical signals in the initial set, respective initial local values of a signal propagation metric at the selected positions for an initial time;
spatially interpolate the initial local values of the signal propagation metric between the selected positions to determine initial interpolated values of the signal propagation metric at intermediate positions, between the selected positions, for the initial time;
acquire a subsequent set of electrical signals from the tissue at the selected positions;
determine, based on the electrical signals in the subsequent set, respective subsequent local values of the signal propagation metric at the selected positions for a subsequent time;
spatially interpolate the subsequent local values of the signal propagation metric between the selected positions to determine subsequent interpolated values of the signal propagation metric at the intermediate positions, for the subsequent time;
generate an initial static frame based on the initial local values and the initial interpolated values;
generate a subsequent static frame based on the subsequent local values and the subsequent interpolated values;
generate dynamic frames based on the initial and subsequent static frames in accordance with a rate of static frame generation, including providing a visual indication in the dynamic frames when a subsequent interpolated value exceeds a bound defined by the rate of static frame generation, wherein the bound is exceeded when a difference between an initial interpolated value of an intermediate position of the initial time and a subsequent interpolated value at the same intermediate position of the subsequent time exceeds the rate of static frame generation; and
energize an ablation electrode to ablate tissue at a location of the heart to alter the tissue conductivity at the location based on the dynamic frames.

7. The apparatus of claim 6, wherein the signal propagation metric comprises a local activation time (LAT) of the selected positions.

8. The apparatus according to claim 6, wherein there are no intervening sets of electrical signals between the subsequent set and the initial set.

9. The apparatus according to claim 6, wherein the processor is configured to:
- acquire a prior set of electrical signals from the selected positions;
- determine, based on the electrical signals in the prior set, respective prior local values of the signal propagation metric at the selected positions for a prior time;
- spatially interpolate the prior local values of the signal propagation metric between the selected positions to determine prior interpolated values of the signal propagation metric at the intermediate positions for the prior time;
- generate a prior static frame based on the prior local values and the prior interpolated values; and
- generate dynamic frames based on the initial and prior static frames, including providing a visual indication in the dynamic frames when an interpolated value exceeds a bound defined by the rate of static frame generation, wherein the bound is defined with respect to the initial interpolated values and the prior interpolated values, wherein the bound is exceeded when a difference between an initial interpolated value of an intermediate position of the initial time and a prior interpolated value at the same intermediate position of the prior time exceeds the rate of static frame generation.

10. The method according to claim 9, wherein there is no intervening set of electrical signals between the prior set and the initial set.

* * * * *